United States Patent
Parida et al.

(10) Patent No.: US 10,607,718 B2
(45) Date of Patent: *Mar. 31, 2020

(54) ALGEBRAIC PHASING OF POLYPLOIDS

(71) Applicant: INTERNATIONAL BUSINESS MACHINES CORPORATION, Armonk, NY (US)

(72) Inventors: Laxmi P. Parida, Mohegan Lake, NY (US); Filippo Utro, Pleasantville, NY (US)

(73) Assignee: INTERNATIONAL BUSINESS MACHINES CORORATION, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/411,292

(22) Filed: May 14, 2019

(65) Prior Publication Data

US 2019/0267111 A1 Aug. 29, 2019

Related U.S. Application Data

(63) Continuation of application No. 16/236,866, filed on Dec. 31, 2018, which is a continuation of application (Continued)

(51) Int. Cl.
*G16B 30/00* (2019.01)
*G16B 20/00* (2019.01)
*G06F 17/16* (2006.01)

(52) U.S. Cl.
CPC ............. *G16B 30/00* (2019.02); *G06F 17/16* (2013.01); *G16B 20/00* (2019.02)

(58) Field of Classification Search
CPC .................. G06F 19/22; G06F 17/16
(Continued)

(56) References Cited

U.S. PATENT DOCUMENTS 6,931,326 B1 8/2005 Judson et al.
7,058,517 B1 6/2006 Denton et al.
(Continued)

FOREIGN PATENT DOCUMENTS

WO 2013103759 A2 7/2013

OTHER PUBLICATIONS

Aguiar, et al. "Haplotype assembly in polyploid genomes and identical by descent shared tracts," Bioinformatics, vol. 29., Jul. 1, 2013 pp. 352-360.

(Continued)

*Primary Examiner* — Tan V Mai
(74) *Attorney, Agent, or Firm* — Cantor Colburn LLP; Vazken Alexanian

(57) ABSTRACT

Embodiments of the present invention include method, systems and computer program products for algebraic phasing of polyploids. Aspects of the invention include receiving a matrix including a set of two or more single-nucleotide poloymorphisms (SNPs) for two or more sample organisms. Each row of the matrix is set to a ploidy based on a number of ploidies present in the two or more sample organisms. Each allele in the set of two or more SNPs is represented as a binary number. A set of algebraic rules is received, wherein the set of algebraic rules include an algebraic phasing algorithm. And the set of algebraic rules are applied to the matrix to determine a haplotype of a parent of the two or more sample organisms.

20 Claims, 15 Drawing Sheets

Related U.S. Application Data

No. 15/810,242, filed on Nov. 13, 2017, now Pat. No. 10,169,531, which is a continuation of application No. 15/597,330, filed on May 17, 2017, now Pat. No. 10,176,296.

(58) Field of Classification Search
USPC .......................................................... 708/520
See application file for complete search history.

(56) References Cited

U.S. PATENT DOCUMENTS

| | | |
|---|---|---|
| 8,673,564 B2 | 3/2014 | Simons |
| 10,169,531 B2 | 1/2019 | Laxmi et al. |
| 10,176,296 B2 | 1/2019 | Laxmi et al. |
| 2003/0099964 A1 | 5/2003 | Patil et al. |
| 2013/0157870 A1 | 6/2013 | Pusfikarev et al. |
| 2015/0120256 A1 | 4/2015 | Huang et al. |
| 2015/0169823 A1 | 6/2015 | Chin |
| 2015/0337298 A1 | 11/2015 | Xi et al. |
| 2015/0363550 A1 | 12/2015 | Green, Jr. et al. |
| 2016/0201124 A1 | 7/2016 | Donahue et al. |
| 2016/0203196 A1 | 7/2016 | Schnall-Levin et al. |
| 2018/0057885 A1 | 3/2018 | Rabinowitz et al. |
| 2019/0139626 A1 | 5/2019 | Laxmi et al. |

OTHER PUBLICATIONS

List of IBM Patents or Patent Applications Treated as Related; (Appendix P), Filed May 14, 2019; 2 pages.

Mazrouee, et al., "HapColor: A graph coloring framework for polyploidy phasing" Bioinformatics and Biomedicine (BIBM), 2015 IEEE International Conference on Year 2015, pp. 105-108.

Mazrouee, Sepideh, "PACH: Ploidy-AgnostiC Haplotyping," Bioinformatics and Biomedicine (BIBM), 2015 IEEE International Conference on Year 2015, pp. 1786-1788.

Shen, et al. "SHEsisPlus, a toolset for genetic studies on polyploid species," www.nature.com/scientificreports, Scientific Reports 6, Published Apr. 6, 2016, pp. 1-10.

Su, et al., "Inference of haplotypic phase and missing genotypes in polyploid organisms and variable copy number genomic regions," BioMed Central, BMC Bioinformatics 9 Published Dec. 1, 2008, pp. 1-9.

| input conds | operation details | comments |
|---|---|---|
| | $X' = \text{res}(X)$ | |
| $x_L \neq \emptyset$ | For each pair $v, \bar{v} \in x_L$, $x'_1 = x_1 + 1, x'_0 = x_0 + 1,$ $x'_L \leftarrow x_L \setminus \{\bar{v}, v\}, x'_I = x_I - 2$ | (clean up of var set $x_L$; can be periodically invoked) $X'_p = X_p$ |

FIG. 4

| input conds | operation details | comments |
|---|---|---|
| | $X' = v2c(k, d, X)$ | |
| $0 \leq k \leq x_l$<br>$d = 0, 1$ | Pick some $k$ vars, $v_1, ..., v_k$ in $x_L$<br>$x'_d = x_d + k$<br>$x'_L = x_L \setminus \{v_1, ..., v_k\}; x'_l = x_l - k$ | (some $k$ vars in $x_L$ are assigned $d$)<br>$\{X'\} \subset \{X\}$<br>$X'_p = X_p$ |

FIG. 5

| input conds | operation details | comments |
|---|---|---|
| | $y'_L = v2v(k, x_L, y_L)$ | |
| $0 \le k \le |x_L|, |y_L|$ | some $k$ vars in $y_L$ are assigned to some $k$ vars in $x_L$. VOID, if no such mapping exists (note a var $v$ can be assigned to itself but not to it's complement) | $x_L$ does not change; $y_L$ is modified, i.e., $k$ vars in $y_L$ are re-labeled, & so are all the upstream instances (Note if $Y$ is the modified $Y$ then $\{Y'\} = \{Y\}; Y'_p = Y_p)$ |

FIG. 6

| input conds | operation details | comments |
|---|---|---|
| | $(X_{new}, Y_{new}) = \text{resVar}(t_{x1}, t_{x0}, t_{y1}, t_{y0}, t_v, X, Y)$ | |
| | Partition $x_L$ and $y_L$ as follows<br>$x_L = S_{x1} \uplus S_{x0} \uplus S_{xv} \uplus S_{xr}$<br>$y_L = S_{y1} \uplus S_{y0} \uplus S_{yv} \uplus S_{yr}$<br>with<br>$|S_{xv}| = |S_{yv}| = t_v$<br>for $d = 0, 1 : |S_{xd}|, |S_{yd}| = t_{xd}, t_{yd}$<br>and $(S_{x1} \cup S_{x0} \cup S_{xv}) \cap (S_{y1} \cup S_{y0} \cup S_{yv}) = \emptyset$.<br><br>IF the above partitioning in not possible<br>THEN resVar() is VOID<br><br>$t_v$ vars in $S_{yv}$ are randomly assigned to vars in $S_{xv}$<br>For $d = 0, 1$ the vars of $S_{xd}$ are assigned $d$<br>For $d = 0, 1$ the vars of $S_{yd}$ are assigned $d$<br>$X_{new} = (x_1 + t_{x1}, x_0 + t_{x0}, S_{xv} \cup S_{xr})$<br>$Y_{new} = (y_1 + t_{y1}, y_0 + t_{y0}, S_{yv} \cup S_{yr})$ | $\uplus$ denotes disjoint union |

FIG. 7

| Z | $Z_1$ | $Z_0$ | $Z_L$ | comments |
|---|---|---|---|---|
| | symmetric & transitive binary operations | | | |
| $X \cup Y$ when $X_p = Y_p$ (randomized) | $\min\{x_1, y_1\}$ | $\min\{x_0, y_0\}$ | $x_L \cup \{q_1, ..., q_k\}$ | if cond I $\{x_1 = y_1\}$ $y'_L = v2v(x_l, x_L, y_l)$ $\|x_1\| = y_1\| = k$ New variables $q_1, ..., q_k$ |
| | | $y_0$ | $y_L$ | if cond II $\{x_1 < y_1 \& X \subseteq Y\}$ $x'_L = v2v(y_l, y_L, x_l)$ |
| | | $x_0$ | $x_L$ | if cond III $\{y_1 < x_1 \& Y \subseteq X\}$ $y'_L = v2v(x_l, x_L, y_l)$ |
| | | VOID (no unique triple notification) | | otherwise |
| $X \cap Y$ | $\min_1$ | $\min_0$ | $x_L \cap y_L$ | $\min_1 = \min\{x_1, y_1\}$ $\min_0 = \min\{x_0, y_0\}$ |
| $X \cap_k Y$ (randomized) | | EMPTY when $Z \equiv (0, 0, \emptyset)$ $\cup_{W_p = k}(W \le (X \cap Y))$ | | $k \le (X \cap Y)$ Note $Z_p = k$ |
| | unary operations | | | |
| $X_{v \leftarrow 1}$ $X_{v \leftarrow 0}$ | $x_1 + 1$ $x_1$ | $x_0$ $x_0 + 1$ | $x_L \setminus \{v\}$ | $Z = v2c(1,1,l/0, X)$ with $v \in x_L$ |
| | asymetric binary operations | | | |
| $X \setminus Y$ when $X_p \ge Y_p$ | $x_1 - y_1 - y'_l$ | $x_0 - y_0 - y'_l$ VOID if $z_1 < 0$ or $z_0 < 0$ | $x'_L \cup \bar{y}_L$ | $x'_L = x_L \setminus (x_L \cap y_L)$ $y'_L = y_L \setminus (x_L \cap y_L)$ $\bar{y}'_L = \{\bar{v}\| v \in y'_L\}$ Note $Z_p = X_p - Y_p$ |

FIG. 8

| | randomized component in $f$ | comments / resolve vars |
|---|---|---|
| $Z = X \cdot_f Y$ | | |
| $X \cap_f Y$ when $X \cap Y$ is EMPTY  $t$ is the desired increase in ploidy of $Z$ | For $d = 0, 1$ $gap_d = y_d - x_d$; $buff_d = x_d - y_d$ $nN(gap_d)$; $nN(buff_d)$ $t$ is randomly split into 3 non-negative integers, i.e. a random point in shaded region of Fig. 1, as $t = (t_{1x} \oplus t_{1y}) + (t_{0x} \oplus t_{0y}) + t_v$ where all the following hold: $t_v \le \min(x_j, y_j)$ $(t_{1x} \oplus t_{0x}) + t_v \le x_j$ $(t_{1y} \oplus t_{0y}) + t_v \le x_j$ and For $d = 0, 1$ IF $y_d - x_d \ge 0$, $t_{dx} \le \min(gap_d, x_j)$; $t_{dy} = 0$ ELSE $t_{dx} = 0$, $t_{dy} \le \min(buff_d, y_j)$ | (force a negative val $v$ to 0) $nN(v) \equiv$ IF $v < 0$ THEN $v \leftarrow 0$ $t_{1x} \oplus t_{1y}$ denotes on of $t_{1x}, t_{1y}$ is positive, but not both Similarly $t_{1y} \oplus t_{0y}$ $(X_{new}, Y_{new}) =$ resVar$(t_{1x}, t_{0x}, t_{1y}, t_{0y}, t_v, X, Y)$ $Z = X_{new} \cap Y_{new}$ $(Z_p = t)$ |
| $X \setminus_f Y$ when $X \setminus Y$ is VOID | (at least $y_f + gap_1 + gap_0$ vars needs to be resolved) $gap_1 + gap_0 \le x_j$ must hold ELSE VOID $y_j$ is randomly split into 3 non-negative integers, i.e. a random point in shaded region of Fig. 1, as $y_j = t_1 + t_0 + t_v$ where the following hold: $t_1 \le buff_1$; $t_0 \le buff_0$ $t_v \le x_j - (gap_1 + gap_0)$ | $x_j, x_L, y_j, y_L$ from $X \setminus Y$ defn $(X_{new}, Y_{new}) =$ resVar$(gap_1, gap_0, t_1, t_0, t_v, X, Y)$ $Z = X_{new} \setminus Y_{new}$ |

FIG. 9

$X \cup Y = (1, 2, 1) = (1, 2, \{q\})$ $X \cap Y = \bigcup \left( 1, 1, \{q\}), (0, 1, \{q\}), (0, 1, 0), (0, 2, 0) \right)$    make var $r$ is lost $= (0, 0, \{a, q\}) \cup (0, 1, \{0\})$    by defn of $\cap$; transitivity $= (0, 0, \{a = b, q\})$    cond I; new vars $a$, $b$ cond III; internal var $a$ can be dropped The next example:

$X \cup Y = (1, 2, 2) = (1, 2, \{r, q\})$ $X \cap Y = \bigcup \left( (1, 1, \{q\}), (0, 2, \{q\}), (1, 1, \{r\}), (0, 2, \{r\}), (0, 1, \{r, q\}), (1, 0, \{r, q\}), (1, 2, 0) \right)$ $= (0, 1, \{a, q\}) \cup (0, 1, \{b, r\}) \cup (0, 1, \{r, q\}) \cup (1, 0, \{r, q\}) \cup (1, 2, 0)$    cond I in both $= (0, 1, \{a = b, q = r\}) \cup (1, 2, 0)$    cond II $= (0, 1, \{a = b, q = r\}) \cup (1, 2, 0)$    discard genotypes whose ploidy<3 due to var identity $r = q$ $= (0, 1, \{a, r = q\})$    cond III; internal new vars $b$, $c$, dropped

| Plant | Ploidy | 1 | 2 | 3 | 4 | 5 |
|---|---|---|---|---|---|---|
| a | 5 | 00000 | 00000 | 00000 | 0011$\bar{z}$ | 00111 |
| d | 5 | 00000 | 11111 | 0111$\bar{x}$ | 0011$\bar{y}$ | 01111 |
| c | 3 | 111 | 11$\bar{s}$ | 111 | 11$\bar{v}$ | 111 |
| b,c | 3 | 111 | 01s | 111 | 01v | 000 |
| b | 2 | 11 | 0$\bar{s}$ | 11 | 0$\bar{v}$ | 00 |
| e | 2 | 11 | 00 | 1$\bar{x}$ | $\bar{y}\bar{z}$ | 00 |
| e,e,b | 1 | 1 | 1 | 1 | 1 | 0 |
| d,e | 1 | 0 | 1 | x | y | 0 |
| a,e | 1 | 0 | 0 | 0 | z | 0 |

1304

| Plant | Ploidy | 1 | 2 | 3 | 4 | 5 |
|---|---|---|---|---|---|---|
| a | 5 | 00000 | 00000 | 00000 | 0011$\bar{z}$ | 00111 |
| d | 5 | 00000 | 11111 | 0111$\bar{x}$ | 0011$\bar{y}$ | 01111 |
| c | 3 | 111 | 11$\bar{s}$ | 111 | 11$\bar{v}$ | 111 |
| b,c | 2 | 11 | 1s | 11 | 1v | 0 |
| e | 2 | 11 | 00 | 1$\bar{x}$ | $\bar{y}\bar{z}$ | 00 |
| b | 1 | 1 | $\bar{s}$ | 1 | $\bar{v}$ | 0 |
| e,e,b | 1 | 1 | 1 | 1 | 1 | 0 |
| d,e | 1 | 0 | 1 | x | y | 0 |
| a,e | 1 | 0 | 0 | 0 | z | 0 |
| b,b,c | 1 | 1 | 0 | 1 | 0 | 0 |

1306

| Plant | Ploidy | 1 | 2 | 3 | 4 | 5 |
|---|---|---|---|---|---|---|
| a | 4 | 0000 | 0000 | 0000 | 01$\bar{z}\bar{z}$ | 0111 |
| d | 5 | 00000 | 11111 | 0111$\bar{x}$ | 0011$\bar{y}$ | 01111 |
| c | 3 | 111 | 11$\bar{s}$ | 111 | 11$\bar{v}$ | 111 |
| b,c | 2 | 11 | 1s | 11 | 1v | 0 |
| e | 2 | 11 | 00 | 1$\bar{x}$ | $\bar{y}\bar{z}$ | 00 |
| b | 1 | 1 | $\bar{s}$ | 1 | $\bar{v}$ | 0 |
| e,e,b | 1 | 1 | 1 | 1 | 1 | 0 |
| d,e | 1 | 0 | 1 | x | y | 0 |
| a,e,a | 1 | 0 | 0 | 0 | z | 0 |
| b,b,c | 1 | 1 | 0 | 1 | 0 | 0 |

1308

| Plant | Ploidy | 1 | 2 | 3 | 4 | 5 |
|---|---|---|---|---|---|---|
| a | 3 | 000 | 000 | 000 | $\bar{z}\bar{z}\bar{z}$ | 111 |
| d | 5 | 00000 | 11111 | 0111$\bar{x}$ | 0011$\bar{y}$ | 01111 |
| c | 3 | 111 | 11$\bar{s}$ | 111 | 11$\bar{v}$ | 111 |
| b,c | 2 | 11 | 1s | 11 | 1v | 0 |
| e | 2 | 11 | 00 | 1$\bar{x}$ | $\bar{y}\bar{z}$ | 00 |
| b | 1 | 1 | $\bar{s}$ | 1 | $\bar{v}$ | 0 |
| e,e,b | 1 | 1 | 1 | 1 | 1 | 0 |
| d,e | 1 | 0 | 1 | x | y | 0 |
| a,e,a,a | 1 | 1 | 0 | 0 | z | 0 |
| b,b,c | 1 | 1 | 0 | 1 | 0 | 0 |

FIG. 13

| Plant | Ploidy | 1 | 2 | 3 | 4 | 5 |
|---|---|---|---|---|---|---|
| c | 1 | 0 | 1 | 1 | 1 | 1 |
| d | 1 | 1 | 0 | 1 | 0 | 1 |
| a = a,a | 1 | 0 | 0 | 0 | 1 | 1 |
| e = b = b,d,b | 1 | 1 | 0 | 1 | 0 | 0 |
| b,d,e | 1 | 1 | 0 | 1 | 1 | 0 |
| e,e,b,d | 1 | 0 | 1 | 0 | 1 | 0 |
| c,e,c | 1 | 0 | 0 | 0 | 1 | 0 |
| a,e,a,a | 1 | 1 | 1 | 1 | 0 | 0 |
| d,d | 1 | 0 | 1 | 1 | 1 | 1 |
| c,c,c | 1 | 0 | 1 | 1 | 0 | 1 |

FIG. 14

ALGEBRAIC PHASING OF POLYPLOIDS

DOMESTIC PRIORITY

This application is a Continuation of U.S. Non-provisional patent application Ser. No. 16/236,866 filed on Dec. 31, 2018, titled "ALGEBRAIC PHASING OF POLYPLOIDS", which claims priority to U.S. Pat. No. 10,169,531 issued on Jan. 1, 2019, titled "ALGEBRAIC PHASING OF POLYPLOIDS", which claims priority to U.S. Pat. No. 10,176,296 issued on Jan. 8, 2019, titled "ALGEBRAIC PHASING OF POLYPLOIDS," assigned to the assignee hereof and expressly incorporated by reference herein.

BACKGROUND

The present invention relates to algebraic phasing, and more specifically, to methods, systems, and computer program products for algebraic phasing of polyploids.

Organisms typically possess multiple copies of the same chromosome. Many species in nature are polyploid, which means the species has 2 or more copies of the same chromosomes. Examples of polyploid species include triploids (e.g., seedless watermelons), tetraploids (e.g., Salmonida fish), pentaploids (e.g., Kenai Birch), hexaploid (e.g., wheat, kiwifruit), octaploids or octoploids (e.g., Acipenser, dahlias), decaploids (e.g., certain strawberries), and dodecaploids (e.g., *Celosia argentea, Spartina angelica,* and *Xenopus ruwenzoriensis*). Polyploidy is common in plants and is also observed in some animals.

SUMMARY

Embodiments of the invention include a computer system for algebraic phasing of polyploids, the computer system for applying algebraic rules to single-nucleotide polymorphisms (SNPs) having a processor configured to perform a method. The method includes receiving a matrix representing a set of two or more single-nucleotide poloymorphisms (SNPs) for two or more sample organisms. Each row of the matrix is set to a ploidy based on a number of ploidies present in the two or more sample organisms. Each allele in the set of two or more SNPs is represented as a binary number. A set of algebraic rules is received, wherein the set of algebraic rules include an algebraic phasing algorithm. And the set of algebraic rules are applied to the matrix to determine a haplotype of a parent of the two or more sample organisms.

Embodiments of the invention also include a computer program product for applying algebraic rules to single-nucleotide polymorphisms (SNPs), the computer program product including a non-transitory computer readable storage medium having computer readable program code embodied therewith. The computer readable program code comprising computer readable program code configured to perform a method. The method includes receiving a matrix representing a set of two or more single-nucleotide poloymorphisms (SNPs) for two or more sample organisms. Each row of the matrix is set to a ploidy based on a number of ploidies present in the two or more sample organisms. Each allele in the set of two or more SNPs is represented as a binary number. A set of algebraic rules is received, wherein the set of algebraic rules include an algebraic phasing algorithm. And the set of algebraic rules are applied to the matrix to determine a haplotype of a parent of the two or more sample organisms.

Embodiments of the invention also include a method for applying algebraic rules to single-nucleotide polymorphisms (SNPs). The method includes receiving a matrix representing a set of two or more single-nucleotide poloymorphisms (SNPs) for two or more sample organisms. Each row of the matrix is set to a ploidy based on a number of ploidies present in the two or more sample organisms. Each allele in the set of two or more SNPs is represented as a binary number. A set of algebraic rules is received, wherein the set of algebraic rules include an algebraic phasing algorithm. And the set of algebraic rules are applied to the matrix to determine a haplotype of a parent of the two or more sample organisms.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

FIG. 4 illustrates an equation for variable resolution according to one or more embodiments of the present invention;

FIG. 5 illustrates an equation for variable-to-constant (v2c) according to one or more embodiments of the present invention;

FIG. 6 illustrates an equation for variable-to-variable (v2v) according to one or more embodiments of the present invention;

FIG. 7 illustrates an equation for the resolution of variables (resVar( )) according to one or more embodiments of the present invention;

FIG. 8 illustrates primitive genotype operations according to one or more embodiments of the present invention;

FIG. 9 illustrates algorithm operations performed when $z_L$ is non-empty according to one or more embodiments of the present invention

FIG. 11 illustrates an illustrative example of a relaxed intersection operation according to one or more embodiments of the present invention;

FIG. 13 illustrates four iterations of the input matrix after application of the algebraic phasing algorithm according to one or more embodiments of the present invention;

FIG. 14 illustrates an end result of the application of the algebraic phasing algorithm to the input matrix resulting in eleven haplotypes with a unique configuration according to one or more embodiments of the present invention.

DETAILED DESCRIPTION

In accordance with one or more embodiments of the invention, methods, systems and computer program products for algebraic phasing of polyploids are provided. A polyploid is an organism that has two or more copies of the same chromosome. For example, a kiwi is a polyploid that has five copies of a chromosome. In agriculture, certain traits of plants are desired over other traits. For example, a kiwi having a larger size and/or is evenly shaped is desirable over a kiwi that is smaller and/or has an oddly shape. Another example is a seedless fruit such as a seedless watermelon. When certain traits are deemed desirable, determining a particular part (or full) chromosome(s) that the trait is descendent from is required for repeating the trait in future progeny.

Determining parent chromosomes possessing desired traits is sometimes referred to as haplotype estimation or haplotype phasing. A haplotype is a group of genes within an organism that was inherited together from a single parent. The word "haplotype" is derived from the word "haploid," which describes cells with only one set of chromosomes, and from the word "genotype," which refers to the genetic makeup of an organism. Haplotype phasing, typically, utilizes a process of statistical estimation of a haplotype from genotype data. In one or more embodiments of the present invention, an algebraic phasing of polyploids to determine haplotypes is performed utilizing a non-naïve algorithm as described herein.

Figure 1:
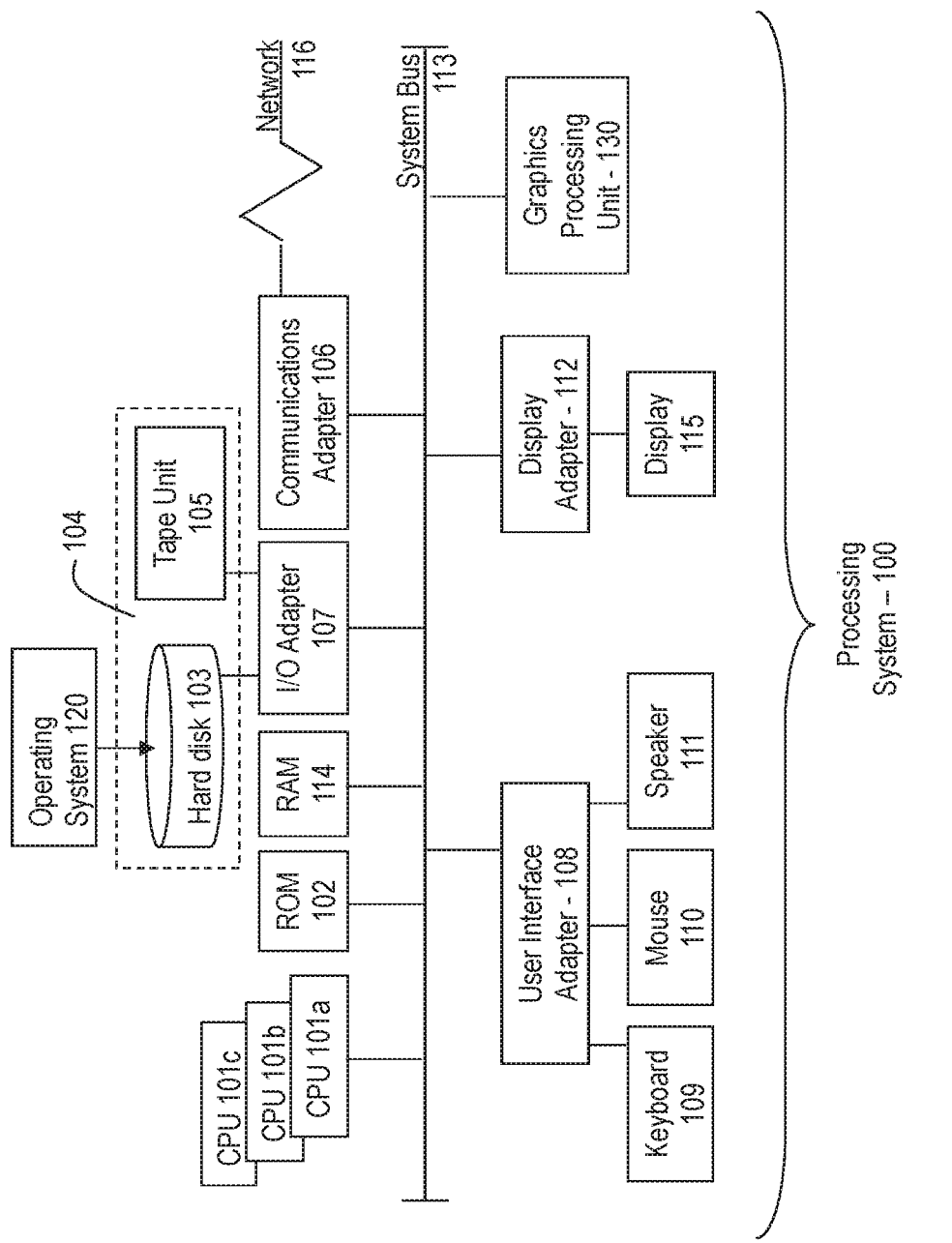
FIG. 1 illustrates a block diagram of a computing system for use in implementing one or more embodiments of the present invention.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 1 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

In exemplary embodiments, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing and has a highly parallel structure that makes it more effective than general-purpose CPUs for algorithms where processing of large blocks of data is done in parallel.

Thus, as configured in FIG. 1, the system 100 includes processing capability in the form of processors 101, storage capability including the system memory 114 and mass storage 104, input means such as keyboard 109 and mouse 110, and output capability including speaker 111 and display 115. In one embodiment, a portion of system memory 114 and mass storage 104 collectively store an operating system coordinate the functions of the various components shown in FIG. 1.

Figure 2:
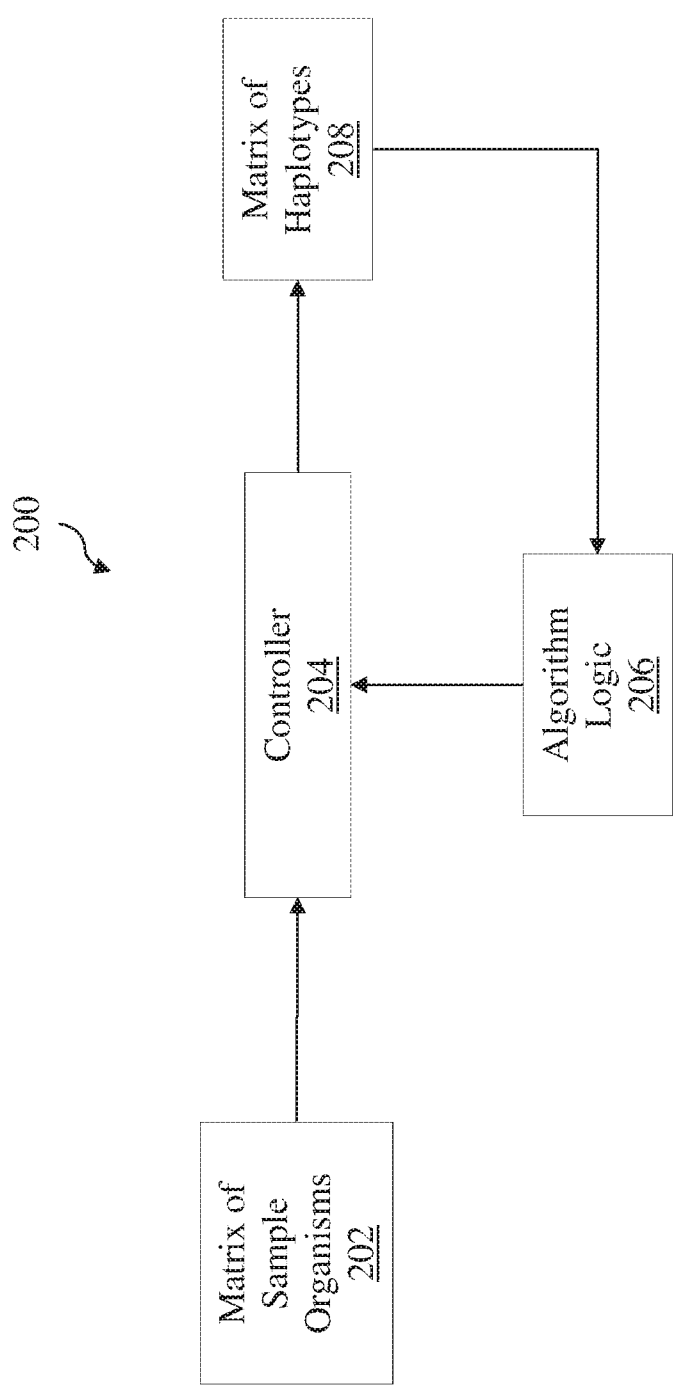
FIG. 2 illustrates a block diagram of a system for algebraic phasing of polyploids according to one or more embodiments of the present invention.

Referring to FIG. 2 there is shown a system 200 for algebraic phasing of polyploids according to one or more embodiments of the invention. The system 200 includes a matrix of sample organisms 202, a controller 204, algorithm logic 206, and a matrix of haplotypes 208, configured and arranged as shown. The system 200 addresses the problem of phasing samples given a matrix of sample organisms 202.

Figure 3:
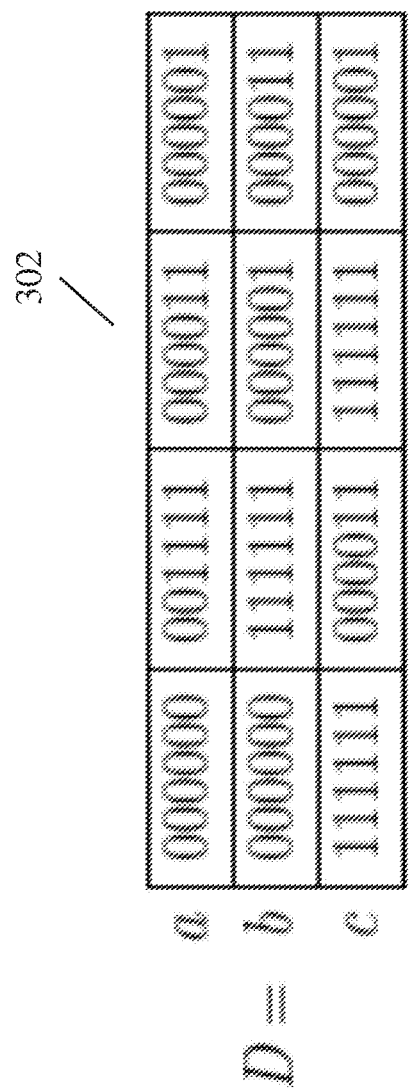
FIG. 3 illustrates an input matrix with three hexaploid organisms according to one or more embodiments of the present invention.

Within the matrix 202, there are rows that denote a sample organism and there are columns that represent an ordered sequence of single-nucleotide polymorphism (SNP). In one or more embodiments of the invention, the SNPs are assumed to be bi-allelic. FIG. 3 depicts an input matrix D 302 with three hexaploid organisms (a, b, c) according to one or more embodiments of the present invention. In each column of the input matrix D, there are single-nucleotide polymorphisms (SNPs) which are represented by either a 0 or a 1. The SNPs show a 0 for a minor allele and a 1 for a major allele. In some embodiments, the SNPs can be represented as a 1 for minor alleles and a 0 for major alleles. The number of 0s and 1s in each column is based on the ploidy of the sample organisms. The organisms in the input matrix 302 are hexaploidy organisms with a total of six 0s and 1s such as 001111 and 000011.

With polyploid phasing, a matrix of sample organisms 202, such as the input matrix D 302, has the algorithm logic applied iteratively until only monoploid rows remain or there is no change in D between one iteration and the next iteration of the algorithm.

Algebraic Phasing Algorithm

The algorithm logic 206 is described below according to one or more embodiments of the present invention. The algorithm logic 206 is utilized to implement the algebraic phasing of polyploids algorithm. An input matrix D, such as the input matrix 302, where each row represents a sample and the ordered columns represent the ordered SNPs is utilized as a representation of a set of SNPs for a multiple organisms (e.g., polyploids). Each entry of the matrix is a genotype of ploid k, i.e., a binary set of size k. The algebraic phasing algorithm resolves the matrix D 302 in to the smallest number of haplotypes (or rows of ploidy 1). An example of the algorithm resolving an input matrix in to the smallest number of haplotypes is found in FIGS. 12-14. A haplotype is a group of genes within an organism that was inherited together from a single parent. The word "haplotype" is derived from the word "haploid," which describes cells with only one set of chromosomes, and from the word "genotype," which refers to the genetic makeup of an organism.

In one or more embodiments of the present invention, the algorithm utilizes the following operations which can be applied in any order.

An input matrix including two or more sample polyploid organisms are initialized by setting the ploidy of each row to be k, the input ploidy and for each ith row, <X>, the set $S^x$ is initialized to the sample represented by that row with multiplicity k. The following algorithm logic 206 (heuristics) is applied until all the rows have ploidy of 1.

Step H-Ia (homozygous SNPs). The algorithm targets homozygous genotypes. The algorithm associates a weight with each ith row as $i_{wt}$ which is computed at every iteration. For instance, a possible weight could be computed as follows: if $i_p$ is 1, the weight is 1, otherwise is computed as the product of the ploidy $i_p$ of the row and the number of homozygous genotypes in the row, $i_h$. Thus $i_{wt}=i_p i_h$. The rows are sorted in decreasing order of the weight and considered for the row operations (as described below). This operation is performed for all ploidies greater than 1 ($i_p>1$).

Step H-IIa (large ploidy from row-row operation ∩). For a pair of rows, carry out the row-row intersection operation ∩ (described below). Note that for this, the ploidy of both the rows is greater than 1. Further, a larger ploidy in the resulting row-row operation is preferred over a smaller ploidy. Should this operation fail, resolve variables using the operation $∩_t^1$ (i.e., t=1).

Step H-IIb (large ploidy from row-row operation \). For a pair of rows, carry out the row-row difference operation \. Further, a larger ploidy in the resulting row-row operation is preferred over a smaller ploidy. If this operation fails, then resolve variables using the operation \$_t$.

Step H-III (resolve variables using input haplotype-constraint). Resolve variables that best fits the input haplotype constraint (external source such as read sequencing data can be used). The preference is to resolve as few variables as possible. A haplotype map describes common patterns of haplotype genetic variations.

Step H-IV (homozygous rows). If none of the above apply, then scan the rows in decreasing order of weight and pick say the ith row <X> with ploidy $i_p>2$. The i row is replaced by a pair of rows:

1. Extract a (random) homozygous diploid row <H> from <X>. $S_H \leftarrow S_x$ and $<H>_p \leftarrow 2$.
2. Let <Z> and <X>\<H>. Then $<Z>_p \leftarrow <X>_p - 2$ and $S_z \leftarrow S_x$, each with multiplicty 2.

The algorithms perform the mentioned steps until input matrix D contains only monoploid or there is no change in D between one iteration and the next iteration. In one or more embodiments of the present invention, the internal steps can be switched to increase the randomness of the process. For example, at iteration i steps H-III can be performed before steps H-IIb. Moreover, the approach also can move directly to the next iteration, after a success of any of the internal steps (H-II).

In one or more embodiments of the present invention, (a) each time that D is updated, its rows can be ordered based on the number of homozygous markers and number of ploidi; and (b) the algorithm can be run several time and the solution provided can be collected to compute statistics and a final consolidated solution can be obtained (e.g., via a majority vote approach).

For application of the above algorithm, the following operations are defined. FIGS. 4-11 illustrate primitive operations defined for practice with the above describe algorithm.

Each element of the input matrix 302 (i.e., each cell) is a genotype, defined as X. Coded genotype X and $x_1$, $x_0$, $x_l$, $x_L$, $X_p$, $\{X\}$ of X are defined below. Each genotype is equivalent to a 3-tuple (triple):

$$X \equiv (x_1, x_0, x_l), \text{ where} \begin{cases} x_1 & \text{number of 1's} \\ x_0 & \text{number of 0's} \\ x_l & \text{number of variables} \\ x_L & \text{is the set of variables and} \\ & x_l = |x_L| \\ X_p & \text{is the ploidy and} \\ & X_p = x_1 + x_0 + x_l \\ \{X\} & \text{set coded by } X \end{cases}$$

The implementation tracks the states of the variables as v or $\bar{v}$ where $v \in x_L$. Some illustrative examples of genotypes according to the above definition are below:

TABLE (1)

| X | 3-tuple | {X} | \|X\| | $X_p$ | $x_L$ |
|---|---|---|---|---|---|
| 11100 | (3, 2, 0) | {11100} | 1 | 5 | ∅ |
| 1110q | (3, 1, 1) | {11100, 11110} | 2 | 5 | {q} |
| 11qr | (2, 0, 2) | {1100, 1110, 1111} | 3 | 4 | {q, r} |

In the illustrated example, the first cell of Matrix D 302 would be defined as (0, 6, 0). The second cell in the first row would be defined as (4, 2, 0). In later examples, variables will be introduced. A coded genotype X is empty when $\{X\}=\emptyset$. X is VOID when $x_1<0$ or $x_0<0$ holds.

Let X and Y be genotypes. $X \leq Y \Leftrightarrow x_1 \leq y_1$, $x_0 \leq y_0$, $x_l \leq y_l$ does not satisfy this condition is invalid (not valid). Complement of a variable v is $\bar{v}$ and $\bar{\bar{v}} = v$. Note that this implies that if $S = x_L \cap y_L$ then S is also valid when $x_L$ and $y_L$ are valid.

For a genotype $X \equiv (x_1, x_0, x_l)$ the following hold:

$|X| = x_l + 1.$ $X \subseteq Y \Leftrightarrow (X_p = Y_p) \text{ AND } y_1 \leq x_1 \leq x_1 + x_l \leq y_1 + y_l.$ Because $X_p = Y_p$, it is adequate to base the arguments only on the number of 1's in X and Y. The possible number of 1's in X is in the interval $[x_1, x_1+x_l]$ and similarly in Y. So if $X \subseteq Y$, then $[x_1, x_1+x_l]$ is contained in $[y_1, y_1+y_l]$ and vice-versa, leading to the above.

⟨X⟩ is defined to an ordered finite list of coded genotypes $X^1, X^2, \ldots, X^j \ldots$ with the same ploidy k. Then k is defined to be $\langle <X> \rangle_p$, the ploidy of the <X>.

Based on the above definition, the resolution of variables is defined in FIG. 4. Additionally, two randomized procedures variable-to-constant (v2c) and variable-to-variable (v2v) are defined in FIG. 5 and FIG. 6. Also, a composition of these two primitive operations in resVar( ) on two coded genotypes and is defined in FIG. 7.

FIG. 4 illustrates an equation for variable resolution according to one or more embodiments of the present invention. This equation is applied where a variable and its complement belong to the same individual or organism making it available to resolve these variables. For example, if x and x̄ belong to the same organism, the complementing nature means it does not matter if x=0, or x=1, because [xx̄] are in the same position for the sample, the result will be [01] because (x=0→x̄=1, and vice versa).

FIG. 5 illustrates an equation for variable-to-constant (v2c) according to one or more embodiments of the present invention. The variable-to-constant equation is further defined in FIG. 8 below.

FIG. 6 illustrates an equation for variable-to-variable (v2v) according to one or more embodiments of the present invention. The variable-to-variable equation is further defined in FIG. 8 below.

FIG. 7 illustrates the equation for resVar( ) according to one or more embodiments of the present invention. In case no extra information is available (or not helpful) to resolve the variable, a random assignment can be applied. These functions provide how in the search space the choice can be randomly selected and relative update of the tuple.

When X and Y are two given genotypes, Z is produced based on the operations defined in FIG. 8. FIG. 8 depicts primitive genotype operations according to one or more embodiments of the present invention.

When a primitive operation fails, i.e., either results in an empty genotype $Z \equiv (0,0, \emptyset)$ or at least one of $z_0$, $z_1$ is negative, variables are resolved by assigning an explicit 1 or 0 (v2c) or assigning the variables to other variables (v2v). In one or more embodiments of the present invention, if $z_L$ is empty, then there is no variable to resolve and this failure cannot be rescued. However, when $z_L$ is non-empty, the operation can be rescued as illustrated in FIG. 9.

FIG. 9 depicts algorithm operations performed when $z_L$ is non-empty according to one or more embodiments of the present invention. These operations correspond to steps H-IIa and H-IIb of the algebraic phasing algorithm.

If $Z = X \cap_k Y$, then $Z_p = k$. And if $Z = X \backslash Y$, then $Z_p = X_p - Y_p$. Note that the union is over genotypes that each has a ploidy of k. Because the union operation maintains the ploidy, the result must hold.

If the operation is not a failure, then the algorithm defines the following:

$$Z_p = z_1 + z_0 + z_l$$
$$= (x_1 - y_1 - y'_l) + (x_0 - y_0 - y'_l) + (x'_l + y'_l)$$
$$= (x_1 + x_0 + x'_l) + (y_1 + y_0 - y'_l)$$
$$= (x_1 + x_0 + x'_l + |x_L \cap y_L|) - (y_1 + y_0 + y'_l + |x_L \cap y_L|)$$
$$= X_p - Y_p$$

Figure 10:
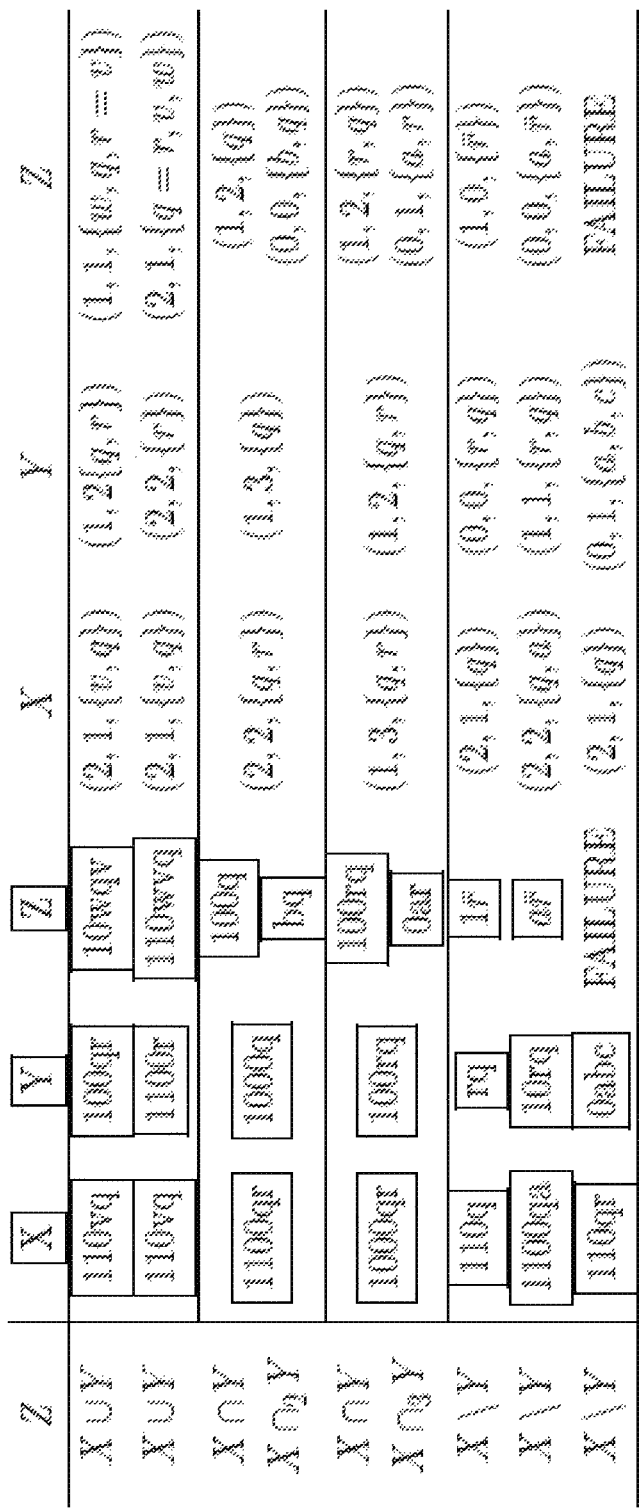
FIG. 10 illustrates primitive operation illustrative examples according to one or more embodiments of the present invention.

FIG. 10 illustrates some primitive operation illustrative examples according to one or more embodiments of the present invention. The operations are shown in the first column under Z and the resultant sets of X, Y, and Z are shown in the next three columns. The tuples for X, Y, and Z are shown in the final columns. With the above definitions of the tuple, the result of X={110vq} corresponds to the tuple of X=(2, 1, 2) or (2, 1, {v, q}).

Any negative value of the tuple is flagged as VOID. FIG. 11 depicts an illustrative example of a relaxed intersection operation according to one or more embodiments of the present invention. The relaxed intersection $X \cap_2 Y$ is carried out as illustrated in FIG. 11. An example intersection operation results in (1, 2, 1) which assigns a variable of {q} as the 1 variable. The relaxed intersection is carried out below taking the union of $\cup_{W_p = k}(W \leq (X \cap Y))$. Where, in the illustrated example, W=(1, 0, {q}), (0, 1, {q}), (1, 1, ∅), (0, 2, ∅). The resulting union operation produces (0, 0, {a, q}) and (0, 1, {b}). These new variables a, b are defined because Condition I is met as illustrated in FIG. 8. A second union operation is performed and the result from the union operation is (0, 0, {a, q}). A variable can be dropped based on Condition III being met as illustrated in FIG. 8.

In the next example in FIG. 11, the relaxed intersection $X \cap_3 Y$ is carried out. An example intersection results in (1, 2, 2) which assigns variable {r, q} as the 2 variables. The relaxed intersection is carried out below taking the union of $\cup_{W_p = k}(W \leq (X \cap Y))$. Where, in the illustrated example, W=(1, 1, {q}), (0, 2, {q}), (1, 1, {r}), (0, 2, {r}), (0, 1, {r, q}), (1, 0, {r, q}), (1, 2, ∅).

If ⟨X⟩ and ⟨Y⟩ are two rows then the intersection and difference operations on <X> and <Y> are defined as:

$$\langle X \rangle \cap \langle Y \rangle = \langle X \cap_k Y \rangle, \text{ where } k = \min_j\{(X^j \cap Y^j)_p\}, \qquad \text{Eq. (1)}$$

$$\langle X \rangle \backslash \langle Y \rangle = \langle X \backslash Y \rangle. \qquad \text{Eq. (2)}$$

For executing the row-row operation (Step H-IIa, Step H-IIb), let $S^x$ be the sample haplotypes associated with ith row say ⟨<X⟩ and $S_y$ be the sample haplotypes associated with i'th row say ⟨Y⟩. Note that the set S tracks mulitplicities as well, i.e., multiple haplotypes of the same sample. In other words if S={a(2), b}, this is interpreted as two haplotypes of sample a and 1 haplotype of sample b.

The row-row operation on <X> and <Y> is defined as follows.

Case I: $X_p > 1$, $Y_p > 1$: The intersection or overlap operation between the two row results in the following three new rows (that replace the ith and i'th rows):
1. ⟨Z⟩ ← ⟨X⟩ ∩ ⟨Y⟩ with $S^z = S_x \cup S_y$, and ⟨Z⟩$_p$ = k, where k is defined in Eqn 1.
2. ⟨V⟩ ← ⟨X⟩ \ ⟨Z⟩ with $S_v = S_x$ and <V>$_p$ = <X>$_p$ - k.
3. ⟨W⟩ ← ⟨Y⟩ \ ⟨Z⟩ with $S^W = S_y$ and <W>$_p$ = <Y>$_p$ - k.

Case II $X_p > 1$, $Y_p = 1$: The intersection or overlap operation between the two row results in the following new row (that replace the ith row):
1. ⟨V⟩ ← ⟨X⟩ \ ⟨Y⟩ with $S_v = S_x$ and <V>$_p$ = <X>$_p$ - 1.
2. $S_y \leftarrow S_y \cup S_x$.

If a row-row operation results in a failure, let X and Y be two genotypes. Then X∩Y is successful, if and only if the following hold.

Case I $X_p > 1$, $Y_p > 1$: None of the following result in EMPTY/VOID: (1) Z=X∩Y, (2) X\Z, and (3) Y\Z.

Case II $X_p > 1$, $Y_p = 1$: X\Y is not VOID. Use "∩$_f$" instead of "∩" and "\$_f$" instead of "\" for the genotype pair when there is EMPTY or VOID result.

Figure 12:
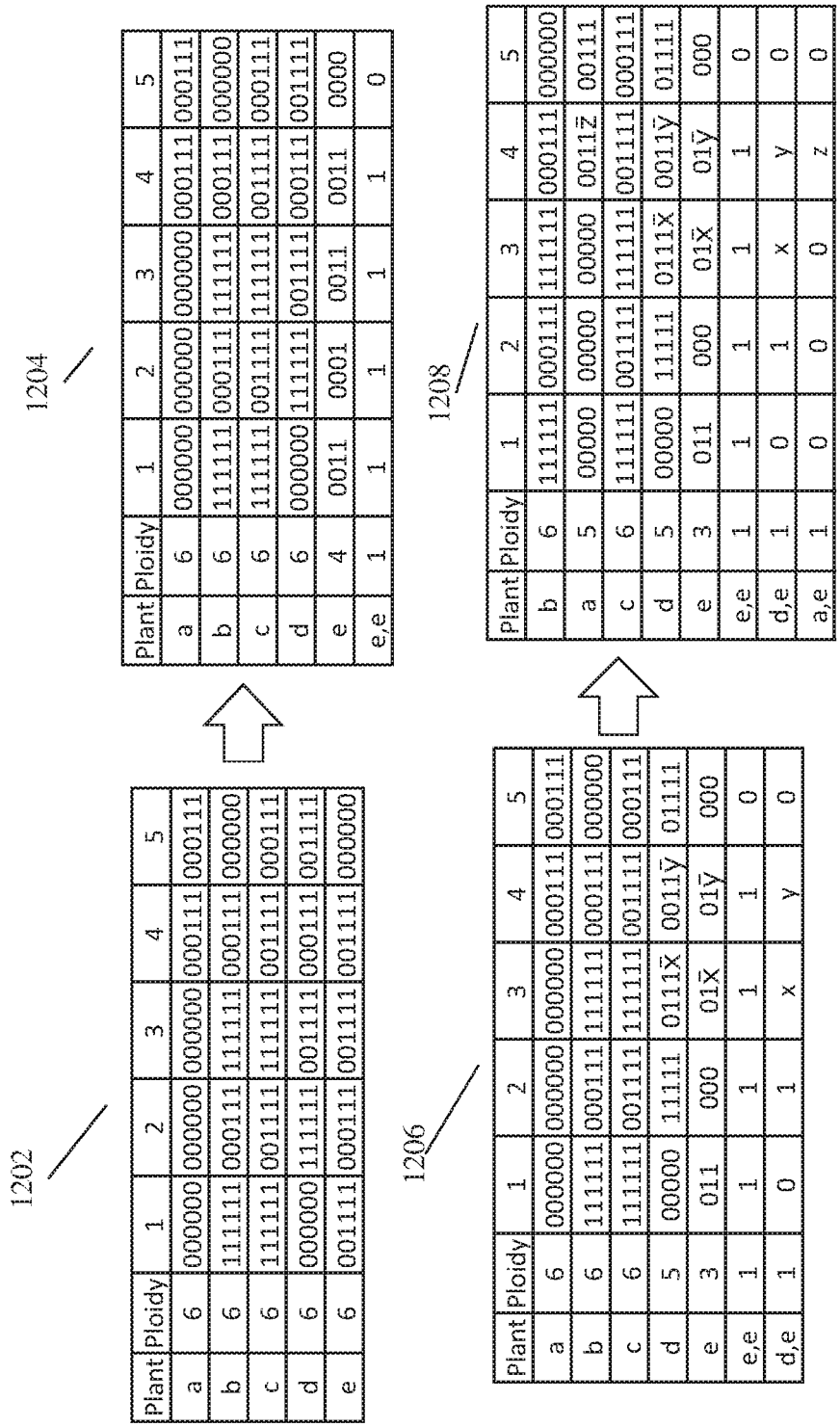
FIG. 12 illustrates an input matrix and three iterations of the matrix after application of the algebraic phasing algorithm according to one or more embodiments of the present invention.

Referring now to FIGS. 12-14 there is shown an illustrated example of an input matrix 1202 representing five markers of five plants and applying the algebraic phasing algorithm to reduce the markers to homozygous alleles of the lowest order ploidy according to one or more embodiments of the present invention.

FIG. 12 illustrates an input matrix 1202 and three iterations 1204, 1206, 1208 of the matrix after application of the algebraic phasing algorithm according to one or more embodiments of the present invention. The input matrix 1202 contains five organisms and five genetic markers. This input matrix 1202 has five hexaploidy organisms (a, b, c, d, and e) with five single-nucleotide polymorphisms (SNPs) shown in columns 1-5. A single-nucleotide polymorphism is a variation in a single nucleotide that occurs at a specific position in the genome, where each variation is present to some appreciable degree within a population. The ploidy at iteration of the algorithm is shown in the second column marked ploidy. Utilizing the above described algorithm, rules are applied to the matrix to find the minimum number of homozygous parents for the input matrix. The goal is to determine the haplotype of the parent of the organisms in the input matrix.

The SNPs are assumed to be bi-allelic. For each column in the input matrix, the nucleic acid bases are coded as 0 or 1. The coding for 0 is for a minor allele. The coding for 1 is for a major allele. In the illustrated example, plant a, in column 1, has six minor alleles in the SNP and in column 5 has three minor alleles and three major alleles.

Applying Step H-Ia to the input matrix 1202, the associated weight of each row has been sorted in decreasing order of weight as defined above. Because plant a has three homozygous genotypes (e.g., [000000]) and a ploidy of 6, the associated weight of plant a's row is 18. Plant b also has a weight of 18 and can be reordered; however, for ease of illustration the plant letters are in order. Plant c has two homozygous genotypes (e.g., [111111]) and a ploidy of 6 giving the row for plant c a weight of 12. The row for plant e has the lowest weight (i.e., 6) and is thus listed last for the input matrix 1202.

The first iteration 1204 applying step H-IIa and step H-IIb to the intersection of row e and row e (or e∩e) from the input matrix 1202 having a resultant row of e,e and e as shown in the first iteration 1204. As described above in the row-row operation, the algorithm defines three new rows of Z, V, and W and the rows of X and Y are both row e of the input matrix 1204. Case I is applied and Z is row e,e and V and W become row e. The operation for Z← is e∩e. The operation for V is e-e,e. And because it is the same row e, the operation for W is e-e,e-e,e with the resultant row e being illustrated in the first iteration 1204. The ploidy for e,e is set at 1 and the ploidy for e is set to 4 because the row-row operation subtracts out k=1 each time the difference operation is performed. Because e had subtracted out e,e twice, the resultant is 6−1−1=4 for the ploidy.

For the second iteration 1206, apply steps H-IIa and H-IIb again to rows d and e from the first iteration 1204. The intersect operation is performed based on the k defined in Eq. 1, where $$k = \min_j \{(X^j \cap Y^j)_p\}.$$

To calculate k, each cell intersect is looked at to see the minimum intersect. For rows d and e, the second cell in each row intersects to result in a k=1. Row d, cell 2 has [111111] and row e, cell 2 has [0001] and the intersect results in [1] resulting in the k=1 per Eq. 1. Cells 1, 3, 4, and 5 result in k=2, 4, 4, and 2, respectively. Per Eq. 1, the minimum ploidy is calculated as k=1. Therefore,⟨X⟩∩⟨Y⟩=⟨X∩₁Y⟩. Case 1 applies here and Z, V, and W are calculated according to the row-row operations. Z=d,e=d∩e, wherein the ploidy of Z is 1. V=d−d,e and the ploidy is 6−1=5. W=e−d,e and the ploidy is 4−1=3.

The intersect operation between row d and row e is performed for each cell of the rows. For cell 1, the intersection results in [00] which is converted to the tuple of (0, 2, Ø). Referring back to FIG. 8, for the case of X∩Y, the mini, mino, and $x_L \cap y_L$ are used to calculate $Z=z_1, z_0$, and $z_L$. Because the ploidy k is equal 1, the min₀=1 and the resulting tuple is (0, 1, Ø) which equates to a cell for row d,e of [0]. As shown in the second iteration 1206, the first cell of row d,e is [0]. Similar steps for cells 2 and 5 are followed to result in the cells containing [1] and [0], respectively.

In the second iteration 1206, for row d,e, cell 3, the resulting cell contains a variable [x]. For this result, the intersection of row d, cell 3 and row e, cell 3 results in [0011] which translates to the tuple of (2, 2, Ø). Referring back to FIG. 8, W is calculated as $\cup_{W_p=k}(W \leq (X \cap Y))$. W ∈ (1, 2, Ø), (2, 1, Ø), (1, 1, Ø), (1, 0, Ø), and (0, 1, Ø). Because k=1, any tuple with a ploidy greater than 1 is removed leaving W ∈ (1, 0,Ø), and (0, 1, Ø). Then the union operation is performed and Condition I is met as illustrated in FIG. 8. Z is calculated as Z=(min {$x_1, y_1$}, min {$x_0, y_0$}, $x_L \cup \{q_1, \ldots, q_k\}$) with $|x_1-y_1|=k=1$. Hence, one new variable is added to result in Z=(0, 0, {x}) which translates to [x] as shown in row d,e, cell 3 of the second iteration 1206.

A similar operation is performed on row d, cell 4 and row e, cell 4 which results in row d,e, cell 4 being [y] as shown in the second iteration 1206. In the row-row operations, the Z row has been calculated as d,e and the V row is calculated as V=d−d,e and the ploidy is 6−1=5. For cells 1, 2 and 5, this calculation includes subtracting out a 0, 1, and 0, respectively for the cells. For cells 3 and 4, having variables x and y, this calculation includes subtracting out a 0 and 1 and adding back x̄ and ȳ. Because the variables x and y can be either 0 or 1, then subtracting out these variables would result in the opposite variables of x̄ and ȳ. For x=1, x̄=0. A similar calculation of W is performed where W=e−d, e with a ploidy of 4−1=3.

FIG. 13 illustrates the fourth 1302, fifth 1304, sixth 1306, and seventh 1308 iteration of the algebraic phasing algorithm according to one or more embodiments of the present invention. For the fourth iteration 1302, steps H-IIa and H-IIb are applied to rows b and row c from the third iteration 1208. The intersect operation is performed based on the k defined in Eq. 1, where $$k = \min_j \{(X^j \cap Y^j)_p\}.$$

To calculate k, each cell intersect is looked at to see the minimum intersect. For rows b and c, the fifth cell in each row intersects to result in a k=3. Row b, cell 5 has [000000] and row c, cell 5 has [000111] and the intersect results in [000] resulting in a k=3 per Eq. 1. Per Eq. 1, the minimum ploidy is calculated as k=3. Thus, row b,c has a ploidy equal to 3 and ⟨X⟩∩⟨Y⟩=⟨X ∩₃ Y⟩. Applying the relaxed intersection from FIG. 11 to each cell of row b and row c, the following results are shown in the fourth iteration of the algorithm 1302. For column 1, the intersection of row b and row c is as follows: [111111]∩[111111]=[111111] which is translated to (6, 0, Ø). Because the ploidy is set at k=3 according to equation 1, the only available tuple is (3, 0, Ø). Hence, the first column of b,c is [111]. Similar steps are taken for columns 3 and 5 resulting in [111] and [000], respectively. For column 2 (and similarly 4), the intersection of row b and c is as follows: [000111]∩[001111]=[00111] which translates to (3, 2, Ø). Because the ploidy is set at k=3 according to equation 1, $\cup_{W_p=k}(W \leq (X \cap Y))$ is applied to derive the following tuples: (2, 1, 0), (1, 2, 0). Applying the union operation defined in FIG. 8, derive Z=X∪Y and Condition 1 applies giving the min{$x_1, y_1$}, min {$x_0, y_0$}, $x_L \cup \{q_1, \ldots, q_k\}$, where $k=|x_1-y_1|$. In this case, k=1, resulting in the introduction of a new variable and the tuple is (1, 1, s) and resulting cell being [01s] for column 2. Following a similar process, column 4 for row b, c is [01v]. The remaining row-row operation is applied where Z row has been calculated as b,c and the V row is calculated as V=c−b,c and the ploidy is 6−3=3. For cells 1, 3 and 5, this calculation includes subtracting out a 111, 111, and 000, respectively for the cells. For cells 2 and 4, because of variables s and v, this calculation includes subtracting out [01] and then subtracting out both a 0 and 1 and adding back $\bar{s}$ and $\bar{v}$. Because the variables s and v can be either 0 or 1, then subtracting out these variables would result in the opposite variables of $\bar{s}$ and $\bar{v}$. For s=1, $\bar{s}$=0.

A similar operation for row b, cell (column) 4 is performed. However, another calculation utilizing row b has been performed in this fourth iteration 1302. The row e,e,b is created with ploidy of 1. The row-row operation for W is now W=b−b,c−e,e,b=[11], [0$\bar{s}$], [11], [$\bar{v}$], [00]. The ploidy is 6−3−1=2.

FIG. 14 depicts an end result of the application of the algebraic phasing algorithm to the input matrix resulting in eleven haplotypes with a unique configuration according to one or more embodiments of the present invention. The final iteration 1402 of the input matrix has eleven rows with a ploidy of 1. The algebraic phasing algorithm is performed on the input matrix until the input matrix contains only monoploid (k=1) or there is no change in the input matrix between one iteration and the next iteration.

For example, each row corresponds to a haplotype and identifies the organism. The first row a haplotype for organism c. The fourth row indicates that one haploid of e is equal to one haploid of b that is also equal to the haploid created by b,d,b. This output reveals the genomic of the parents and can be used in several contexts, such as breeding, genome wide associate studies (GWAS), and pedigree identification.

Figure 15:
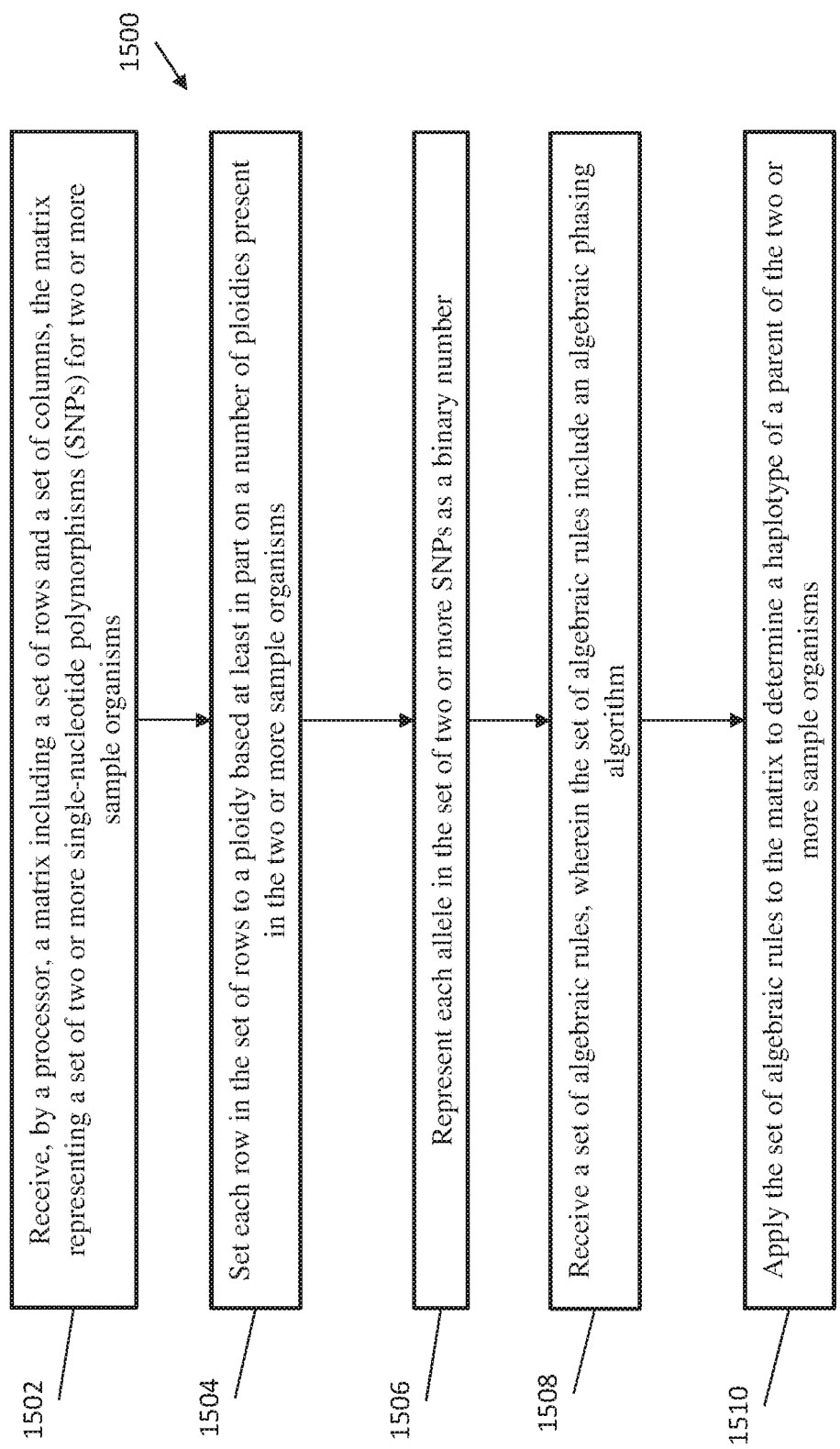
FIG. 15 illustrates a flow diagram of a method for applying algebraic rules to single-nucleotide polymorphisms (SNPs) in accordance with an embodiment.

Referring now to FIG. 15 there is shown a flow diagram of a method 1500 for applying algebraic rules to single-nucleotide polymorphisms (SNPs) according to one or more embodiments of the present invention. At block 1502, the method 1500 includes receiving, by a processor, a matrix including a set of rows and a set of columns, the matrix representing a set of two or more SNPs for two or more sample organisms. The method 1500, at block 1504, includes setting each row in the set of rows to a ploidy based on a number of ploidies present in the two or more sample organisms. At block 1506, the method 1500 includes representing each allele in the set of two or more SNPs as a binary number. Algebraic rules are received in this method 1500, wherein the set of algebraic rules includes an algebraic phasing algorithm as shown at block 1508. At block 1510, the method 1500 includes applying the set of algebraic rules to the matrix to determine a haplotype of a parent of the two or more sample organisms.

Additional processes can also be included. It should be understood that the processes depicted in FIG. 15 represent illustrations, and that other processes can be added or existing processes can be removed, modified, or rearranged without departing from the scope and spirit of the present invention.

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for applying algebraic rules to single-nucleotide polymorphisms (SNPs), the method comprising:
   receiving, by a processor, a matrix comprising a set of rows and a set of columns, the matrix representing a set of two or more SNPs for two or more sample organisms;
   setting each row in the set of rows to a ploidy based on a number of ploidies present in the two or more sample organisms;
   determining a set of algebraic rules; and
   applying the set of algebraic rules to the matrix to determine a haplotype of a parent of the two or more sample organisms.

2. The method of claim 1, wherein each of the two or more sample organisms is a polyploid.

3. The method of claim 1, wherein the ploidy for each of the two or more sample organisms is equal.

4. The method of claim 1 further comprising representing each allele in the set of two or more SNPs as a zero for a minor allele.

5. The method of claim 1, further comprising representing each allele in the set of two or more SNP as one for a major allele.

6. The method of claim 1, wherein the set of algebraic rules comprises:
   a row intersect operation for a first row and a second row in the matrix to determine a minimum ploidy value;
   performing a relaxed intersection on the first row and the second row, wherein the relaxed intersection is defined by the minimum ploidy value; and
   creating a first new row for the matrix based at least in part on a result of the relaxed intersection on the first row and the second row.

7. The method of claim 6, wherein the set of algebraic rules further comprises:
   performing a row difference operation for the first row and the first new row to create a second new row;
   performing a row difference operation for the second row and the first new row to create a third new row;
   replacing the first row with the second new row; and
   replacing the second row with the third new row.

8. The method of claim 1, wherein the set of algebraic rules comprises:
   selecting a row in the matrix with a ploidy greater than two;
   extracting a homozygous diploid row from the row;
   replace the selected row in the matrix with two rows comprising:
      a first row comprising an intersection of the homozygous diploid row and the selected row, wherein a ploidy of the first row is the ploidy of the selected row minus two; and
      a second row comprising a difference of the selected row and the homozygous diploid row.

9. The method of claim 1, wherein the set of algebraic rules are applied to the matrix until all rows of the matrix have a ploidy of one.

10. The method of claim 1, wherein the set of algebraic rules are applied to the matrix until no change occurs between one iteration of the algorithm and a next iteration of the algorithm.

11. A computer system for applying algebraic rules to single-nucleotide polymorphisms (SNPs), the computer system including a processor communicatively coupled to a memory, the processor configured to:
   receive a matrix comprising a set of rows and a set of columns, the matrix representing a set of two or more SNPs for two or more sample organisms;
   set each row in the set of rows to a ploidy based on a number of ploidies present in the two or more sample organisms;
   determine a set of algebraic rules; and
   apply the set of algebraic rules to the matrix to determine a haplotype of a parent of the two or more sample organisms.

12. The system of claim 11, wherein each of the two or more sample organisms is a polyploid.

13. The system of claim 11, wherein the set of algebraic rules comprises:

a row intersect operation for a first row and a second row in the matrix to determine a minimum ploidy value;

performing a relaxed intersection on the first row and the second row, wherein the relaxed intersection is defined by the minimum ploidy value; and creating a first new row for the matrix based at least in part on a result of the relaxed intersection on the first row and the second row.

14. The system of claim 13, wherein the set of algebraic rules further comprises:

performing a row difference operation for the first row and the first new row to create a second new row;

performing a row difference operation for the second row and the first new row to create a third new row;

replacing the first row with the second new row; and replacing the second row with the third new row.

15. The system of claim 11, wherein the set of algebraic rules comprises:

selecting a row in the matrix with a ploidy greater than two;

extracting a homozygous diploid row from the row;

replace the selected row in the matrix with two rows comprising:

a first row comprising an intersection of the homozygous diploid row and the selected row, wherein a ploidy of the first row is the ploidy of the selected row minus two; and a second row comprising a difference of the selected row and the homozygous diploid row.

16. A computer program product for applying algebraic rules to single-nucleotide polymorphisms (SNPs), the computer program product comprising a computer readable storage medium having program instructions embodied therewith, the program instructions executable by a processor to cause the processor to perform:

receiving, by the processor, a matrix comprising a set of rows and a set of columns, the matrix representing a set of two or more SNPs for two or more sample organisms;

setting each row in the set of rows to a ploidy based on a number of ploidies present in the two or more sample organisms;

determine a set of algebraic rules; and applying the set of algebraic rules to the matrix to determine a haplotype of a parent of the two or more sample organisms.

17. The computer program product of claim 16, wherein the set of algebraic rules comprises:

a row intersect operation for a first row and a second row in the matrix to determine a minimum ploidy value;

performing a relaxed intersection on the first row and the second row, wherein the relaxed intersection is defined by the minimum ploidy value; and creating a first new row for the matrix based at least in part on a result of the relaxed intersection on the first row and the second row.

18. The computer program product of claim 17, wherein the set of algebraic rules further comprises:

performing a row difference operation for the first row and the first new row to create a second new row;

performing a row difference operation for the second row and the first new row to create a third new row;

replacing the first row with the second new row; and replacing the second row with the third new row.

19. The computer program product of claim 16, wherein the set of algebraic rules comprises:

selecting a row in the matrix with a ploidy greater than two;

extracting a homozygous diploid row from the row;

replace the selected row in the matrix with two rows comprising:

a first row comprising an intersection of the homozygous diploid row and the selected row, wherein a ploidy of the first row is the ploidy of the selected row minus two; and a second row comprising a difference of the selected row and the homozygous diploid row.

20. The computer program product of claim 16, wherein the set of algebraic rules are applied to the matrix until all rows of the matrix have a ploidy of one.

* * * * *